United States Patent
Smital et al.

(10) Patent No.: US 11,229,403 B2
(45) Date of Patent: Jan. 25, 2022

(54) SYSTEM AND METHOD FOR ASSESSING PHYSIOLOGICAL SIGNAL QUALITY

(71) Applicant: MAYO FOUNDATION FOR MEDICAL EDUCATION AND RESEARCH, Rochester, MN (US)

(72) Inventors: Lukas Smital, Brno (CZ); David R. Holmes, III, Rochester, MN (US); Clifton R. Haider, Rochester, MN (US); Barry K. Gilbert, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 172 days.

(21) Appl. No.: 16/478,539

(22) PCT Filed: Jan. 16, 2018

(86) PCT No.: PCT/US2018/013767
§ 371 (c)(1),
(2) Date: Jul. 17, 2019

(87) PCT Pub. No.: WO2018/136379
PCT Pub. Date: Jul. 26, 2018

(65) Prior Publication Data
US 2020/0037961 A1     Feb. 6, 2020

Related U.S. Application Data

(60) Provisional application No. 62/447,241, filed on Jan. 17, 2017.

(51) Int. Cl.
*A61B 5/00* (2006.01)
*A61B 5/366* (2021.01)

(52) U.S. Cl.
CPC ............ *A61B 5/7221* (2013.01); *A61B 5/366* (2021.01); *A61B 5/7203* (2013.01); *A61B 5/726* (2013.01); *A61B 5/7257* (2013.01)

(58) Field of Classification Search
None
See application file for complete search history.

(56) References Cited

U.S. PATENT DOCUMENTS

| | | |
|---|---|---|
| 2004/0138540 A1 | 7/2004 | Baker et al. |
| 2006/0135860 A1 | 6/2006 | Baker et al. |
| 2011/0004069 A1* | 1/2011 | Ochs .................. A61B 5/02416 600/300 |

(Continued)

OTHER PUBLICATIONS

Choi H and Baraniuk R, Analysis of Wavelet-Domain Wiener Filters, Dept. of Electrical and Computer Engineering, Rice University, Houston TX 77251-1892 USA; IEEE Xplore; https://ieeexplore.ieee.org (Year: 1998).*

(Continued)

*Primary Examiner* — Brian T Gedeon
(74) *Attorney, Agent, or Firm* — Quarles & Brady LLP

(57) ABSTRACT

Systems and methods are provided for evaluating physiological signal quality. A physiological signal, based on a series measurements on a subject, may be received. A quality of the physiological signal received may be evaluated, and an analysis of the physiological signal may be based at least in part on the quality evaluation.

20 Claims, 7 Drawing Sheets

(56) References Cited

U.S. PATENT DOCUMENTS

| | | | |
|---|---|---|---|
| 2012/0016249 A1* | 1/2012 | Lian | A61B 5/349 600/509 |
| 2012/0029320 A1 | 2/2012 | Watson et al. | |
| 2013/0289424 A1* | 10/2013 | Brockway | A61B 5/352 600/509 |
| 2013/0338519 A1 | 12/2013 | Chen et al. | |

OTHER PUBLICATIONS

International Search Report and Written Opinion from parent PCT/US18/13767, dated May 1, 2018, 9 pages.
Alesanco A. et al., "Automatic real-time ECG coding methodology guaranteeing signal interpretation quality," Biomedical Engineering, IEEE Transactions on, vol. 55, pp. 2519-2527, 2008.
Allen J. et al., "Assessing ECG signal quality on a coronary care unit," Physiological measurement, vol. 17, p. 249, 1996.
Bartolo, A. et al., "An arrhythmia detector and heart rate estimator for overnight polysomnography studies," Biomedical Engineering, IEEE Transactions on, vol. 48, pp. 513-521, 2001.
Chiang, Y. et al., "Incorporating a priori knowledge into hidden Markov models for inadequate ECG detection," Computing in Cardiology, vol. 38, 2011. Abstract Only.
Clavier, L. et al., "Automatic P-wave analysis of patients prone to atrial fibrillation," Medical and Biological Engineering and Computing, vol. 40, pp. 63-71, 2002.
Del Rio, B. et al., "Assessment of different methods to estimate electrocardiogram signal quality," in Computing in Cardiology, 2011, 2011, pp. 609-612.
Elghazzawi Z. et al., "A knowledge-based system for arrhythmia detection," in Computers in Cardiology, 1996, 1996, pp. 541-544.
Farina D. et al., "A novel approach for precise simulation of the EMG signal detected by surface electrodes," Biomedical Engineering, IEEE Transactions on, vol. 48, pp. 637-646, 2001.
Farina D. et al., "Comparison of algorithms for estimation of EMG variables during voluntary isometric contractions," Journal of Electromyography and Kinesiology, vol. 10, pp. 337-349, 2000.
Gaziano T. A., "Cardiovascular disease in the developing world and its cost-effective management," Circulation, vol. 112, pp. 3547-3553, 2005.
Gilbert, B. K. et al., "A Measurement-Quality Body-Worn Sensor-Agnostic Physiological Monitor for Biomedical Applications," American Journal of Biomedical Engineering, vol. 5, pp. 34-66, 2015.
Hayn, D. et al., "Real-time visualization of signal quality during mobile ECG recording," Contribution sent to the 38th Physionet Cardiology Challenge, 2011.
Hurd, W. J. et al, "Tri-axial accelerometer analysis techniques for evaluating functional use of the extremities," Journal of Electromyography and Kinesiology, vol. 23, pp. 924-929, 2013.
Iravanian S. et al, "A novel algorithm for cardiac biosignal filtering based on filtered residue method," Biomedical Engineering, IEEE Transactions on, vol. 49, pp. 1310-1317, 2002.
Karmakar, C. K. et al, "Power spectral analysis of ECG signals during obstructive sleep apnoea hypopnoea epochs," in Intelligent Sensors, Sensor Networks and Information, 2007. ISSNIP 2007. 3rd International Conference on, 2007, pp. 573-576.
Kestler, H. et al., "De-noising of high-resolution ECG signals by combining the discrete wavelet transform with the Wiener filter," in Computers in Cardiology 1998, 1998, pp. 233-236.
Kim Y. et al, "Wearable ecg monitor: Evaluation and experimental analysis," in Information Science and Applications (ICISA), 2011 International Conference on, 2011, pp. 1-5.
Kligfield, P. et al., "Recommendations for the standardization and interpretation of the electrocardiogram: part I: the electrocardiogram and its technology a scientific statement from the American Heart Association Electrocardiography and Arrhythmias Committee, Council on Clinical Cardiology; the American College of Cardiology Foundation; and the Heart Rhythm Society endorsed by the International Society for Computerized Electrocardiology," Journal of the American College of Cardiology, vol. 49, pp. 1109-1127, 2007.
Kohler et al. in "The principles of software QRS detection," Engineering in Medicine and Biology Magazine, IEEE, vol. 21, pp. 42-57, 2002.
Kuzilek, J. et al., "Data driven approach to ECG signal quality assessment using multistep SVM classification," in Computing in Cardiology, 2011, 2011, pp. 453-455.
Lander P. et al., "Time-frequency plane Wiener filtering of the high-resolution ECG: Background and time-frequency representations," Biomedical Engineering, IEEE Transactions on, vol. 44, pp. 247-255, 1997.
Li Q. et al., "Artificial arterial blood pressure artifact models and an evaluation of a robust blood pressure and heart rate estimator," Biomedical engineering online, vol. 8, p. 13, 2009.
Li Q. et al., "Robust heart rate estimation from multiple asynchronous noisy sources using signal quality indices and a Kalman filter," Physiological measurement, vol. 29, p. 15, 2008.
Li Q. et al., "Signal quality indices and data fusion for determining acceptability of electrocardiograms collected in noisy ambulatory environments," Computing in Cardiology, vol. 38, 2011.
Lin, C. et al., "P-and T-wave delineation in ECG signals using a Bayesian approach and a partially collapsed Gibbs sampler," Biomedical Engineering, IEEE Transactions on, vol. 57, pp. 2840-2849, 2010.
Lugade, V. et al., "Validity of using tri-axial accelerometers to measure human movement—Part I: Posture and movement detection," Medical engineering & physics, vol. 36, pp. 169-176, 2014.
Mukhopadhyay S. C., "Wearable sensors for human activity monitoring: A review," Sensors Journal, IEEE, vol. 15, pp. 1321-1330, 2015.
Orphanidou, C. et al., "Signal-quality indices for the electrocardiogram and photoplethysmogram: derivation and applications to wireless monitoring," IEEE journal of biomedical and health informatics, vol. 19, p. 832, 2015.
Schwab, D. J. et al., "A Measurement-Quality Body-Worn Physiological Monitor for Use in Harsh Environments," American Journal of Biomedical Engineering, vol. 4, pp. 88-100, 2014.
Shwedyk, E. et al., "A nonstationary model for the electromyogram," Biomedical Engineering, IEEE Transactions on, pp. 417-424, 1977.
Silva, I. et al., "Improving the quality of ECGs collected using mobile phones: The Physionet/Computing in Cardiology Challenge 2011," in Computing in Cardiology, 2011, 2011, pp. 273-276.
Smital, L. et al., "Adaptive wavelet Wiener filtering of ECG signals," Biomedical Engineering, IEEE Transactions on, vol. 60, pp. 437-445, 2013.
Sukor, J. A. et al., "Signal quality measures for pulse oximetry through waveform morphology analysis," Physiological measurement, vol. 32, p. 369, 2011.
Tat, T. H. C. et al, "Physionet challenge 2011: improving the quality of electrocardiography data collected using real time QRS-complex and T-wave detection," in Computing in Cardiology, 2011, 2011, pp. 441-444.
Thakor N. V., "From Holter monitors to automatic defibrillators: developments in ambulatory arrhythmia monitoring," Biomedical Engineering, IEEE Transactions on, pp. 770-778, 1984.
Tsien C. L. et al., "Poor prognosis for existing monitors in the intensive care unit," Critical care medicine, vol. 25, pp. 614-619, 1997.
Verrier, R. L., et al., "Ambulatory Electrocardiogram-Based Tracking of T Wave Alternans in Postmyocardial Infarction Patients to Assess Risk of Cardiac Arrest or Arrhythmic Death," Journal of cardiovascular electrophysiology, vol. 14, pp. 705-711, 2003.
Vitek M et al., "Detection of QRS boundaries and T wave end in multilead ECG signals," in Proceedings of the 14th Conference Student EEICT 2008, 2008, pp. 285-289.
Vitek M., "Automatické rozmerení signálu EKG," Vysoké ucení technické v Brne. Fakulta elektrotechniky a komunikacních technologií, 2011. With English Abstract.
Wang, J. "A new method for evaluating ECG signal quality for multi-lead arrhythmia analysis," in Computers in Cardiology, 2002, 2002, pp. 85-88.

(56) References Cited

OTHER PUBLICATIONS

Willems J., "Recommendations for measurement standards in quantitative electrocardiography," European Heart Journal, vol. 6, pp. 815-825, 1985.

Willems, J. L. et al., "Establishment of a reference library for evaluating computer ECG measurement programs," Computers and biomedical research, vol. 18, pp. 439-457, 1985.

Xia, H. et al., "A multistage computer test algorithm for improving the quality of ECGs," Contribution sent to the 38th Physionet Cardiology Challenge, 2011.

Zidelmal, Z. et al, "QRS detection using S-Transform and Shannon energy," Computer methods and programs in biomedicine, vol. 116, pp. 1-9, 2014.

* cited by examiner

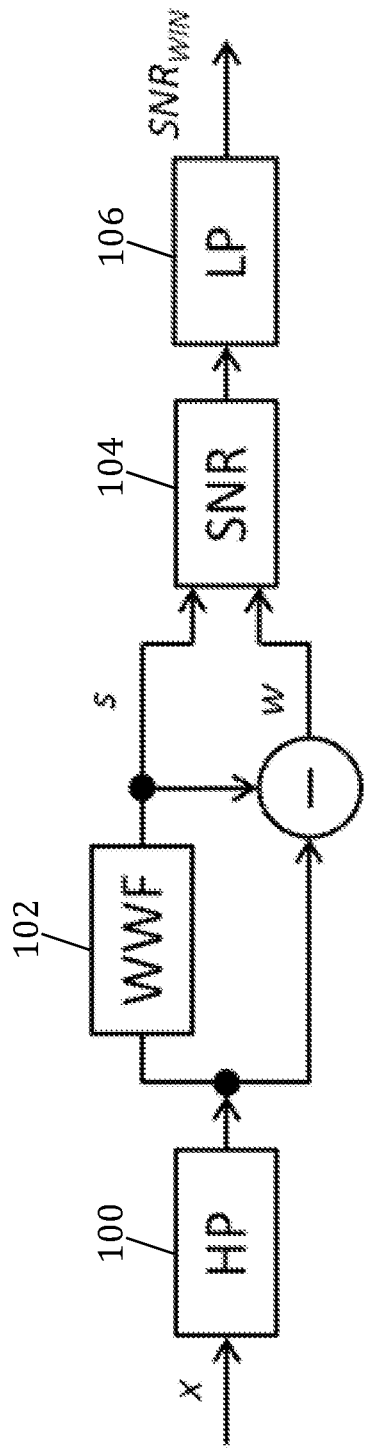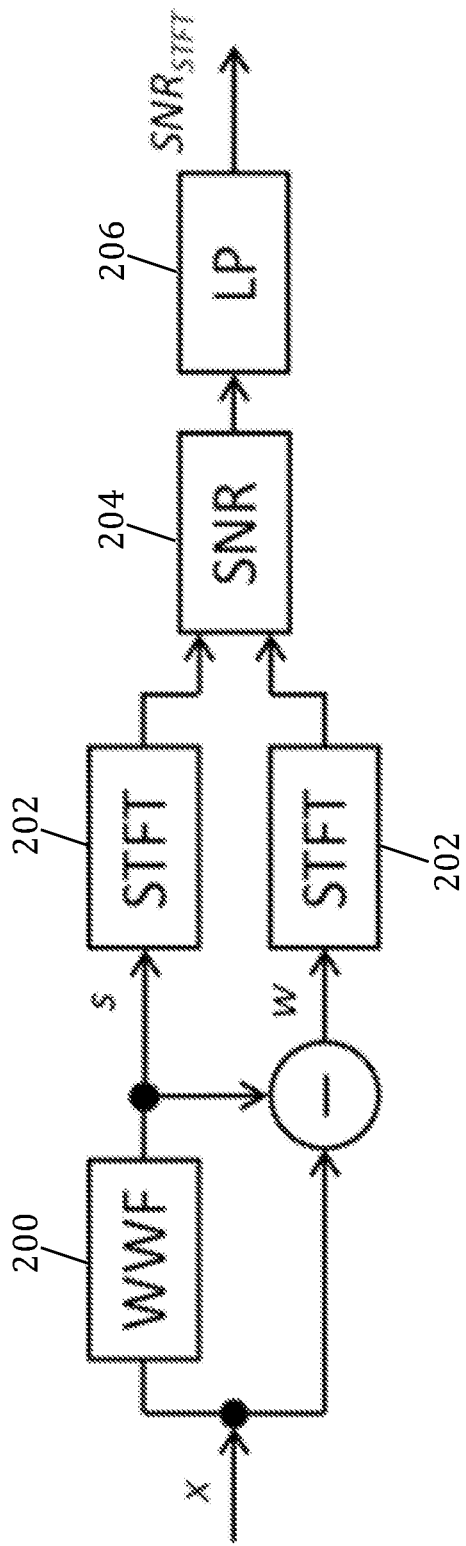
Fig. 1
Fig. 2

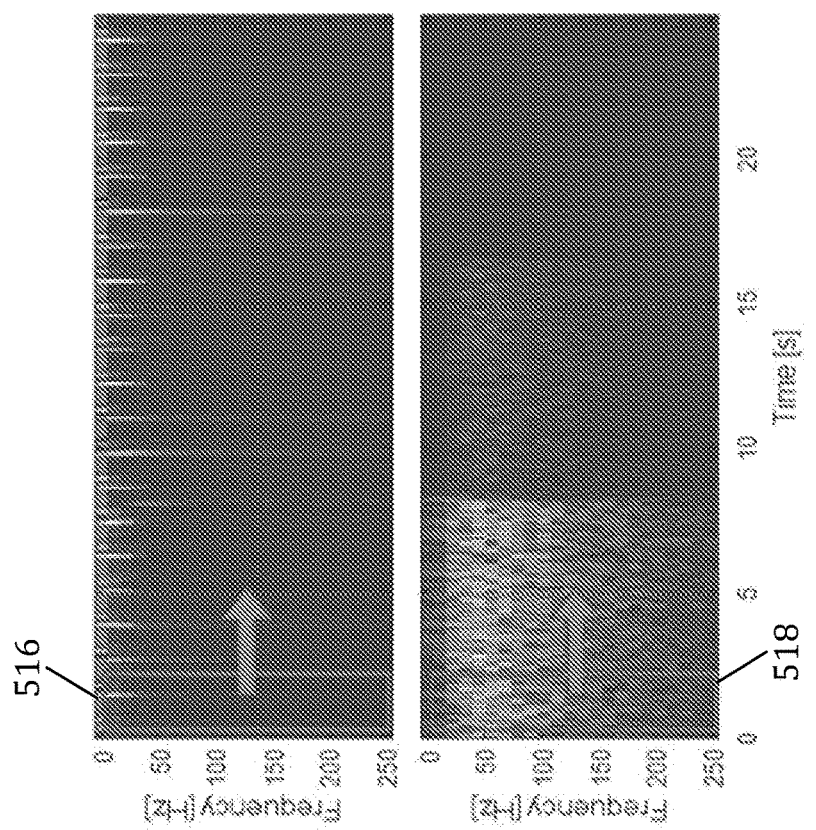
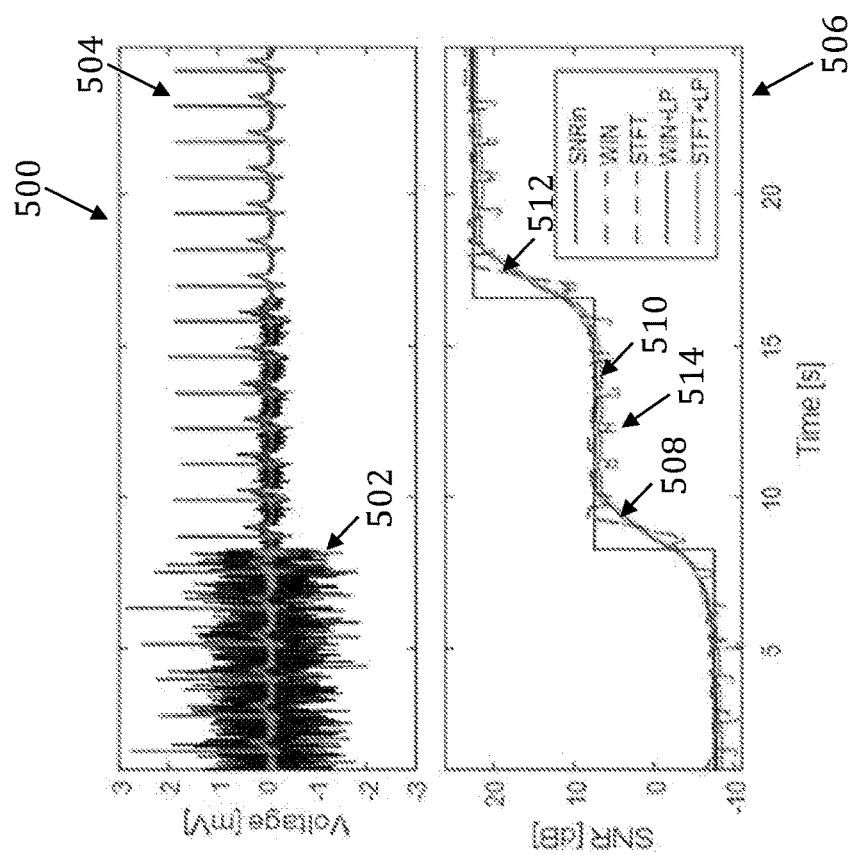
Fig. 5A
Fig. 5B

SYSTEM AND METHOD FOR ASSESSING PHYSIOLOGICAL SIGNAL QUALITY

CROSS-REFERENCE TO RELATED APPLICATIONS

This application is a 371 U.S. National Phase Entry of PCT/US2018/013767, filed Jan. 16, 2018, which claims priority to U.S. Provisional Application No. 62/447,241, filed Jan. 17, 2017, and entitled "SYSTEM AND METHOD FOR ASSESSING PHYSIOLOGICAL SIGNAL QUALITY." These applications are incorporated herein by reference as if set forth in their entireties for all purposes.

FIELD OF THE DISCLOSURE

This disclosure relates to the evaluation of the quality of physiological readings, and more specifically to the assessment of physiologic signals (such as electrocardiogram (ECG) signals) and variable analysis of signals based on quality assessment.

BACKGROUND

Cardiovascular diseases (CVD) are the leading cause of death worldwide. Some studies note that approximately 30% of all deaths worldwide are associated with CVD; in developing countries, CVD may be disproportionally higher. The most common diagnostic method used to detect heart disease is measuring the heart's electrical activity by electrocardiography (ECG). But not all ECG signals are of the same quality, and long-term ECG monitoring data often contain a variety of artifacts (e.g., powerline interference, drift, impulse noise, and muscle noise) that complicate subsequent analysis. The change in noise intensity over time and overall non-stationarity of the signal can also complicate the processing of the long-term signal. If signals are analyzed without discrimination, or otherwise not effectively selected based on their quality or acceptability, the quality of the analysis (and potentially a diagnosis) could suffer. Moreover, if all signals are processed, even ones that lack usable readings, additional computing resources are used unnecessarily, something that is of particular concern with portable devices or other applications with limitations in processing power. Real-time signal quality estimation can help with suppressing false alarms, detecting sensor misplacement (and potentially, making adjustments to device, sensor, or lead placement as needed), selecting segments to extract clinically relevant features, or defining parameters for further processing. Previous approaches to quality estimation have involved review of statistical or morphological features from signals, such as review of successive QRS complexes, RR interval lengths, arterial blood pressure, and ECG signal amplitudes.

Although ECG analysis is a well-accepted CV monitoring approach, its use has been limited to in-clinic studies and Holter monitoring for discrete clinical studies. As consumer-grade and clinical-grade wearable technologies become more commonplace, the need for remote monitoring is also likely to increase. A recent review of the field of consumer- and clinical-grade health monitors has noted that the market could grow to $20 billion by 2017. The value of wearable technologies is directly related to the quality of meaningful findings they generate. Given the relatively limited processing power and data storage capacity of wearable technologies, and the magnitude of the data the devices generate, better evaluation of ECG signal quality would tend to make the devices more useful and their results more reliable.

What is needed is a system and method for effectively evaluating the quality of the ECG signal prior to analysis and, based on signal quality, more intelligently route segments of the ECG signal for different levels/types of additional analysis. Such a system would help mitigate the need to analyze (all of the) massive amounts of data collected by, for example, wearable devices, or any device in which processing power might be limited or in which the quality of readings received does not remain constant. Estimating quality before further analysis can be especially useful to long-term recording by Holter monitors and other experimental devices.

SUMMARY

The present disclosure provides exemplary systems and methods for estimating signal quality based on a quality metric such as a ratio of the noise-free signal power to noise power ("signal-to-noise ratio," or SNR). A noise-free signal can be estimated using (for example) a Wiener Filter, such as a Wavelet Wiener Filter (WWF). The SNR may be calculated in either the time domain or frequency domain. In either domain, the calculation may be performed in a sliding window of specified length, allowing for real-time processing. The systems and methods may also involve segmenting a physiological signal according to a quality metric, and subsequently applying different processing methods to individual segments. In this way, complicated analysis of poor-quality data can be avoided, and data can be processed using algorithms that are tuned to the signal quality. Further advantages and features of the invention will be apparent from the remainder of this document in conjunction with the associated drawings.

In accordance with one aspect of the disclosure, a method is provided for evaluating signal quality. The method includes receiving a physiological signal based on a series measurements on a subject, evaluating a quality of the physiological signal received, and, basing an analysis of the physiological signal at least in part on the quality evaluation.

In accordance with another aspect of the disclosure, a system is provided for evaluating electrocardiographic (ECG) signal quality. The system includes a processor executing instructions that cause the processor to receive a physiological signal based on a series measurements on a subject, evaluate a quality of the physiological signal received, and base an analysis of the physiological signal at least in part on the quality evaluation.

In accordance with another aspect of the disclosure, a method is provided for evaluating electrocardiographic (ECG) signal quality. The method includes receiving ECG signals based on readings of electrical activity in the heart of a subject, determining an ECG signal power for the ECG signals received, and calculating a quality metric based on the power of the ECG signals received.

In accordance with another aspect of the disclosure, a system is provided for evaluating electrocardiographic (ECG) signal quality. The system includes a processor executing instructions for receiving ECG signals based on readings of electrical activity in the heart of a subject, determining an ECG signal power for the ECG signals received, and calculating a quality metric based on the power of the ECG signals received.

In accordance with another aspect of the disclosure, a method is provided for evaluating signal quality in real time. The method includes receiving ECG signals based on readings of electrical activity in the heart of a subject, determining a quality metric for the ECG signals received, and basing analysis of the ECG signals on changes in the quality metric.

In accordance with another aspect of the disclosure, a method is provided for evaluating signal quality in real time. The method includes using an ECG device to measure electrical activity in the heart of a subject to obtain ECG signals, calculating a quality metric for the ECG signals, and determining an analysis level based on the quality metric.

In accordance with another aspect of the disclosure, a system is provided for evaluating signal quality in real time. The system includes an ECG device for measuring electrical activity in the heart of a subject and providing ECG signals and a processor configured to calculate a quality metric for the ECG signals and determine an analysis level based on the quality metric in real time.

Other aspects of the disclosure will be made apparent from the disclosure.

BRIEF DESCRIPTION OF THE DRAWINGS

FIG. 1 is a block diagram of an exemplary signal quality estimation process using a sliding window approach.

FIG. 2 is a block diagram of an exemplary signal quality estimation process using a short time Fourier transform (STFT) frequency approach.

FIG. 5A shows, an artificial ECG signal with changing noise level and estimates of noise-free signal by wavelet Wiener filter (WWF) correlated with a comparison for signal-to-noise ratio (SNR) curve calculation in the time domain and frequency domain, without (dashed line) and with (solid line) LP filtering.

FIG. 5B shows a spectrogram of estimated noise-free signal calculated by the WWF correlated with a spectrogram of noise FIG. 6A provides a graph that shows that sensitivity (Se) and positive predictive value (P+) depend on SNR for QRS complex detection.

DETAILED DISCUSSION

Figure 3:
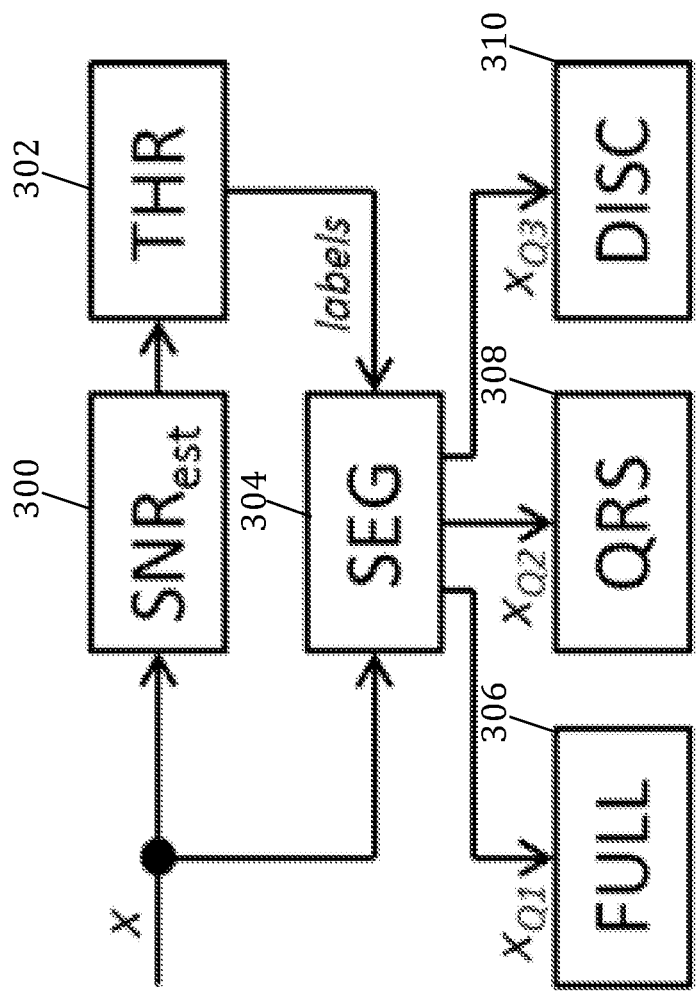
FIG. 3 is a block diagram showing an exemplary signal processing process for segments of varying quality.

Defining a quality metric is useful in evaluating the quality of a physiological signal (i.e., a series of measurements) acquired via, for example, electrocardiography (ECG), electromyography (EMG), blood oxygenation level dependent (BOLD) imaging in functional magnetic resonance imaging (fMRI), photoplethysmography (PPG), and the like. To classify quality, a quality metric such the signal-to-noise ratio (SNR) of the signal itself can be estimated using an estimate of the noise-free signal. This quality metric allows for determination of the accuracy or value of physiological signal analysis at various quality levels (e.g., with respect to ECG signals analysis, the ability to identify a QRS complex given a particular signal SNR). In the ECG context, the system can indicate, for example, when (a relatively more computationally-demanding) complete full wave analysis versus (a relatively less computationally-demanding) QRS detection are feasible based on the SNR signal. It is noted that exemplary ECG signal analyses are provided below and in the drawings as non-limiting applications of the exemplary systems and methods discussed in the present disclosure.

In estimating SNR, the examined digital signal x[n] can be treated as an additive mixture of noise-free signal s[n] and noise w[n], according to the equation x[n]=s[n]+w[n], where n represents the digital time sequence. Improving the estimation of the noise-free signal improves the calculation of SNR. To estimate the noise-free signal, a Wavelet Wiener Filter method (WWF)—a two-stage algorithm operating in the wavelet domain—can be used. In the first stage of the WWF, thresholding of the wavelet coefficients is used to estimate the noise-free signal coefficients $u_m[n]$. The details of threshold selection and reconstruction are described in L. Smital, M. Vítek, J. i. Kozumplík, and I. Provazník, "Adaptive wavelet Wiener filtering of ECG signals," *Biomedical Engineering, IEEE Transactions on*, vol. 60, pp. 437-445, 2013.

In the second stage, a Wiener correction factor $g_m[n]$ is computed according to equation (1), and the input (noisy) coefficients $y_m[n]$ are adjusted according to equation (2):

$$g_m(n) = \frac{u_m^2(n)}{u_m^2(n) + \sigma_m^2(n)}, \tag{1}$$

$$\tilde{y}_m(n) = y_m(n)g_m(n), \tag{2}$$

where $\sigma^2_m[n]$ is the variance of the noise coefficients in the m-th frequency band and $\tilde{y}_m[n]$ is the estimation of the denoised wavelet coefficients. After processing is completed in the wavelet domain, the final result can be transformed into the time domain to determine the denoised output signal.

By subtracting the noise-free signal estimate from the input signal, the estimated noise in the input signal can be computed. To compute the local SNR signal, one of at least two approaches can be used for SNR estimation after separating the noise and signal components: 1) a time-based sliding window approach; and 2) a short time Fourier transform (STFT) frequency approach.

One non-limiting example of an implementation of the sliding window approach is illustrated in the block diagram in FIG. 1, which uses time-domain processing. A high pass filter 100 used for initial processing is added to remove the components of the input signal of frequencies below 0.67 Hz (primarily those attributed to baseline wander, movement, and respiration), for example, which can influence the accuracy of SNR calculation. As described above, a WWF block 102 can be included followed by an SNR block 104. In the SNR block 104, the local energy of the noise-free signal s[n] and noise w[n] bounded by windows (W) with a length of two seconds can be computed. The SNR estimated by the sliding window approach ($SNR_{win}$) is computed in decibels according to equation (3):

$$SNR_{win}[n] = 10\log_{10}\left(\frac{\sum_{j=n-W/2}^{n+W/2}(s[j])^2}{\sum_{j=n-W/2}^{n+W/2}(w[j])^2}\right) dB. \quad (3)$$

A low pass filter block 106 can be included before the $SNR_{win}$ is delivered.

Referring to FIG. 2, second non-limiting approach for estimating SNR is based on the STFT, is provided. Again the input signal, x, can be fed to a WWF block 200 to deliver the noise-free signal, s, and the noise signal, w, to respective STFT block 202. The STFT blocks 202 estimate the local frequency content and creates a matrix representing the development of the spectrum over time, which will be called the spectrogram (SG).

The noise power and the noise-free signal is computed in block SNR 204, such that the noise power and the noise-free signal are estimated from the area in the spectrograms between frequencies $f_1$ (e.g., 0.67 Hz) and $f_2=f_s/2$, where $f_s$ denotes the sampling frequency. This frequency range covers the dominant frequency content of the ECG signal and muscle noise, the most common broadband interference to corrupt the ECG signal. A floating window (W) with a length of two seconds can be used for power estimation. The SNR estimated by the STFT approach ($SNR_{STFT}$) is computed using equation (4):

$$SNR_{STFT}[n] = 10\log_{10}\left(\frac{\sum_{i=f_1}^{f_2}\sum_{j=n-W/2}^{n+W/2}(SG_s[i,j])^2}{\sum_{i=f_1}^{f_2}\sum_{j=n-W/2}^{n+W/2}(SG_w[i,j])^2}\right) dB, \quad (4)$$

where $SG_s$ and $SG_w$ are the spectrograms of the noise-free signal and the noise, respectively.

Due to the fixed window size of W, the estimate of SNR is variable according to the number of QRS complexes within the window. Accordingly, for both approaches the SNR estimate is averaged afterwards, in LP block, 106, 206, in another window of the same length.

By measuring the quality of the ECG signal continuously, it can be determined which segments of the signal are suitable for further processing and which are not. However, before the signal is divided into different segments according to quality, the quality classes of interest are defined. A suitable definition of quality classes may be, as a non-limiting example: (Q1) segments that exhibit low noise levels and allow full ECG wave analysis; (Q2) segments that contain higher levels of noise (than Q1) but can be processed reliably for QRS detection; and (Q3) segments that contain exceedingly high levels of noise that preclude further meaningful processing.

FIG. 3 illustrates a signal processing pipeline that can be used to determine ECG signal segments of varying quality. The input signal, x, is fed into an $SNR_{est}$ block 300, which represents the SNR estimation algorithm shown above in FIGS. 1 and 2. This feeds into a THR block 302 that tracks the continuous SNR curve and produces classified labels used for segmentation of the input signal in an SEG block 304, where segmentation proceeds according to the received labels. Individual segments of the input signal are further processed according to their quality.

Figure 4:
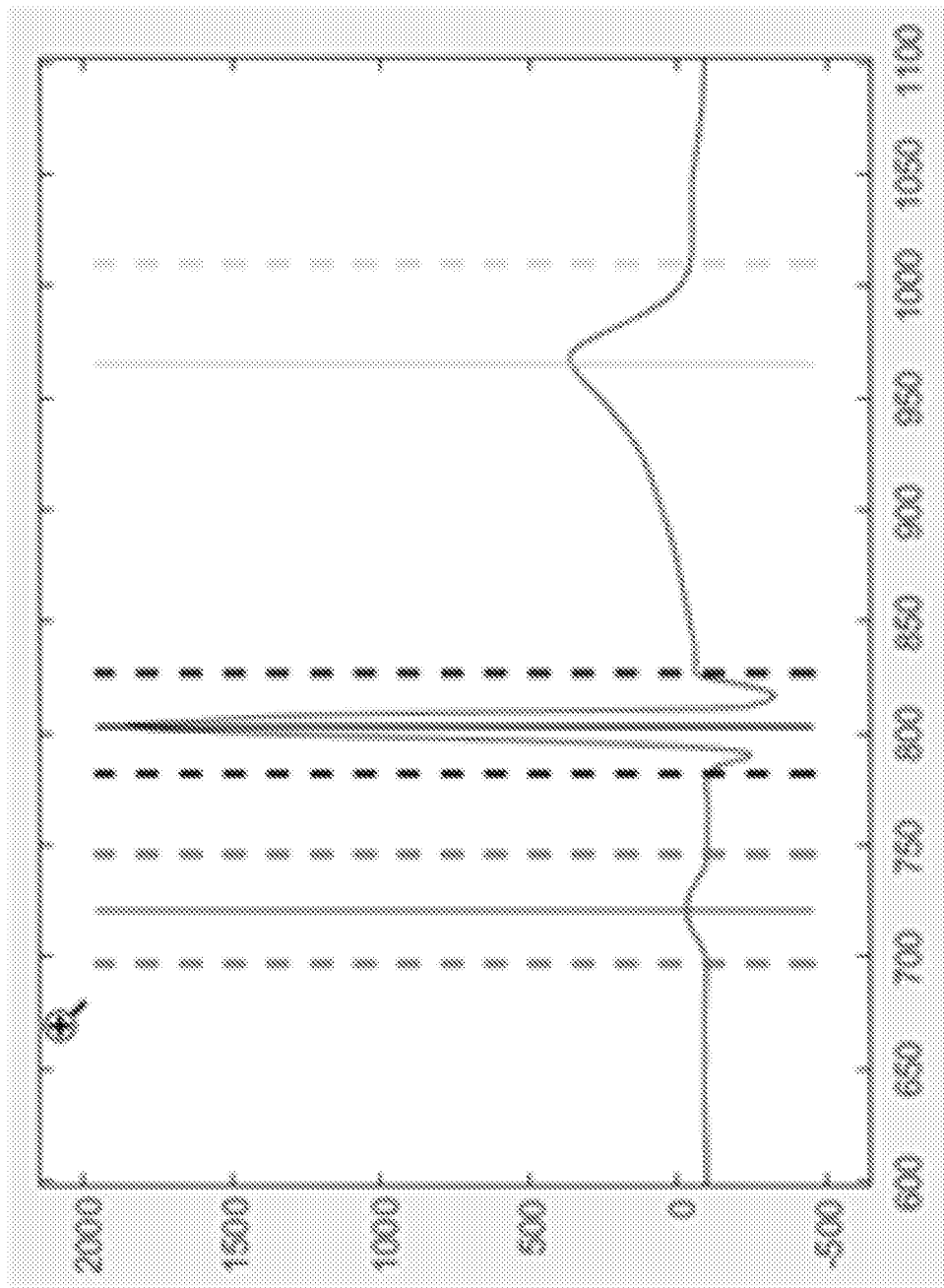
FIG. 4 shows five significant points delineated on an artificial ECG curve used for validation: P onset, P offset, QRS onset, QRS offset, and T offset.

Specifically, quantifying (in decibels of SNR) the differences in threshold levels between the quality classes is important to the process of defining Q1, Q2, and Q3. A full ECG waveform analysis block 306 receives the Q1 segments allow reliable detection of the QRS complex and five other significant points in the ECG curve, as illustrated in FIG. 4. A QRS block 308 is designed to deliver reliable detection of the QRS segment, which satisfies the criteria for quality class Q2. QRS detection is considered successful if the sensitivity and positive predictive value are greater than a threshold, such as 99.5%. Detection accuracy below the threshold can be used as a differentiator for a DISC block 310 that selects the quality class Q3. These thresholds between quality classes were determined using an artificial model of an ECG signal and artificial EMG noise, as further discussed below. The thresholds can be adjusted and varied as desired to suit particular applications.

The signal quality estimate can be used to delineate the three classes. An ECG segmentation algorithm (e.g. the process of labeling a dataset with Q1, Q2, and Q3) can include two steps: basic segmentation and correction. The basic segmentation can naively label temporal segments solely on the basis of the thresholds selected for the Q1, Q2, and Q3 classes. These thresholds mark the end of one segment and the beginning of another, and because the SNR level can change rapidly (particularly during motion), the length of each labeled section may be quite variable. Accordingly, correction rules may be applied to retain only those segments that are suitable for subsequent analysis.

There are at least two separate sets of correction rules that may be employed: for example, a first for when a generally high SNR signal falls within an otherwise low SNR signal segment, and a second for when a generally low SNR signal falls within an otherwise high SNR signal segment. In the first case, when a high SNR signal is, for example, shorter than 15 seconds, or its average SNR value is, for example, within one decibel (dB) of the label threshold, the segment can be ignored (i.e., labeled as low SNR similar to adjacent segments). In contrast, for a low SNR segment that is, for example, shorter than two seconds, or where the average SNR value is within, for example, one dB of the label threshold, the low SNR signal is treated as if it were a high SNR signal. This sort of correction can be used to eliminate short segments of signals that are higher in quality than neighboring segments but which are nonetheless not considered suitable for further analysis. Conversely, such correction can be used to eliminate short segments of signals that are of lower quality than neighboring segments, but which are deemed acceptable or desirable for analysis.

Two different ECG datasets have been used to test the algorithms. The first is an artificial ECG dataset for which the required noise level can be set. The second is a dataset acquired from an IRB-approved volunteer study that used a specially designed wearable ECG device. For the artificial ECG dataset, an artificial model of a noise-free signal was corrupted with artificial noise. As a model of an ECG signal, one cycle of a filtered real ECG signal from the "Common Standards for Quantitative Electrocardiography" database—which contains very high quality waveforms with little noise (e.g., see FIG. 4)—was used. By repeating this cycle, an artificial noise-free ECG signal of variable length was obtained. In the design of this model, the approaches used were validated in the literature, in which the typical power spectral density of surface muscle noise is described. The artificial noise was generated by filtering white Gaussian noise through a digital filter with frequency characteristics similar to the power spectra of muscle noise. The final signal-to-noise ratio was obtained by adjusting the amplitude of the noise, as described by Smital et al. (cited above).

For the dataset acquired from a volunteer study, a custom physiologic monitoring platform was used to collect high-resolution ECG data during activity. The platform includes a one-lead configuration for high resolution ECG data collection. The device incorporated a custom low power (100 µW at a 2.8 V supply voltage) ECG circuit with 100 dB common mode rejection. In addition, to capture posture and physical activity, each device also contained 2 g (VTI Technologies, CMA3000-A01) and 16 g tri-axial accelerometers (Analog Devices, ADXL326BCPZ). The device data acquisition rates for both ECG and motion are programmable, and were set to 400 samples per second for the ECG monitor and 10 samples per second per individual x-, y-, and z-axis, respectively. This device configuration allows continuous recording for 14 days on a single 750 mAH battery (Bi-power, BL-7PN-S2).

The artificial model of the ECG signal and the artificial EMG noise discussed above can be useful in illustrating the functionality of SNR estimators. EMG noise can be generated with a gradually changing level, as demonstrated in at graph 500 FIG. 5A. The graph 500 of FIG. 5A shows an artificial ECG signal with changing noise level 502 and estimates of noise-free signal by wavelet Wiener filter (WWF) 504 This graph 500 is correlated with a second graph 506 providing a comparison for signal-to-noise ratio (SNR) curve calculation in the time domain 508 and frequency domain 510, without (dashed line) 512 and with (solid line) 514 LP filtering. In FIG. 5A, three noise levels consistent with noise observed in real data were chosen: −7.5 dB for large interference, 7.5 dB for moderate interference, and 22.5 dB for low interference.

FIG. 5B shows spectrograms used for SNR estimation by the STFT frequency approach. The rectangles 516, 518 indicates the two-second floating window used for calculating signal power. The spectrogram of the noise-free signal in the top panel shows no significant change over time, as it is an estimate of an artificial ECG. In the bottom panel of FIG. 5B, a plot of the residual noise spectrogram shows two clear changes of energy corresponding to the level of generated noise that causes a step change in the estimated SNR curve. The bottom panel of FIG. 5A shows the true noise level, as well as results of both estimation methods.

As shown in the bottom panel of FIG. 5A, there is a cyclic, low-amplitude component to the SNR signal. Variability in the SNR estimation is related to the fixed window size W (=2 sec) and a variable number of QRS complexes within the window. This variability can be removed by LP filtration at the end of the processing chain, as shown in the bottom panel of FIG. 5A. As can be seen, both estimators yield approximately equal results, and both are similar to the preset noise level. Estimates of the SNR vary most from the true SNR at the artificial transitions between SNR levels. SNR can be better estimated for rapidly changing SNR levels by dynamically adjusting the window size according to features within the data.

Figure 6B:
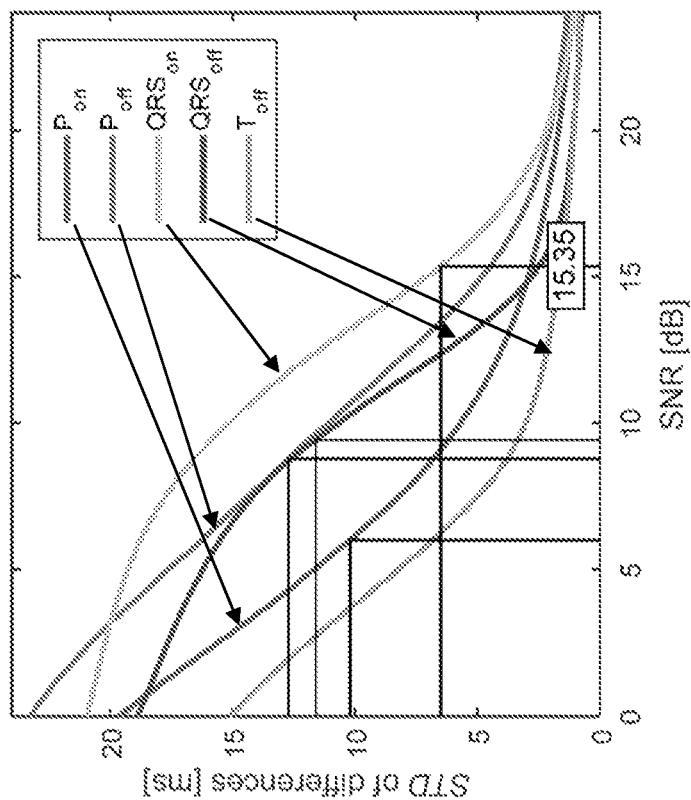
FIG. 6B provides a graph that shows that the standard deviation (STD) of differences depends on SNR for other significant points.
Figure 6A:
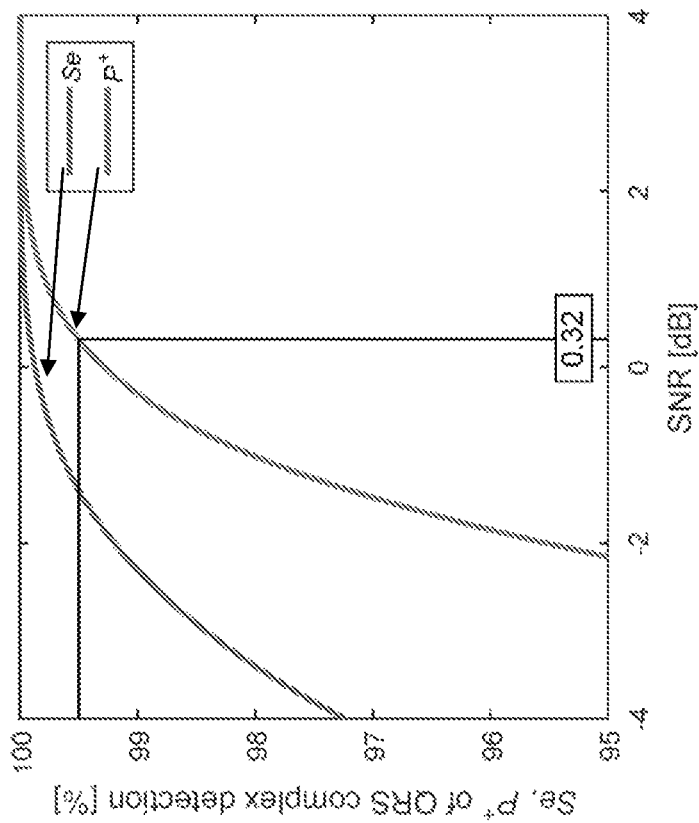

QRS complex detection and ECG delineation were used to search for the thresholds (in decibels of SNR) between different quality classes. To test the ability of a software implementation to detect these boundaries in an artificial ECG dataset, artificial muscle noise was added. In this testing procedure, the SNR was gradually increased in the artificial mixture, and six significant points in the ECG waveform were sought. For each step of SNR, an artificial mixture with 104 RR intervals was generated. In equation (5) below, detection accuracy is expressed by the sensitivity (Se) and positive predictive value (P+) for the QRS complex position and by the standard deviation (STD) of the differences (between reference and detected positions) for other significant points. These statistical parameters are defined respectively as:

$$Se = \frac{TP}{TP+FN}, P^+ = \frac{TP}{TP+FP}, \quad (5)$$

where TP represents true positive values (correctly detected points), FN represents false negative values (undetected points), and FP represents false positive values (incorrectly detected points). The detected position is identified as TP when there is a reference position within the 50 ms tolerance window. (Certain tolerance windows normally used for QRS detection were obtained from Z. Zidelmal, A. Amirou, D. Ould-Abdeslam, A. Moukadem, and A. Dieterlen, "QRS detection using S-Transform and Shannon energy," *Computer methods and programs in biomedicine*, vol. 116, pp. 1-9, 2014.) FIGS. 6A and 6B shows the curve obtained by plotting these statistics according to the SNR of the artificial mixture.

As these curves demonstrate, the detection accuracy of all of the points increases as the noise level in the signal decreases. As noted above, detection of the QRS complex is considered sufficient in this example if both Se and P+ are greater than 99.5%. Both of these conditions are satisfied if the ratio of the power of the SNR is greater than 0.32 dB. Accurate delineation of other significant points in the ECG waveform is more sensitive to the quantity of noise. The detection of significant points is considered successful if the standard deviation of differences between the reference and detected positions is less than the criteria specified in Table I (below). In this scenario, satisfying all of the conditions in Table I is possible only if the SNR is greater than 15.35 dB, as illustrated in FIG. 6B.

TABLE I

CRITERIA 2sCSE FOR STANDARD DEVIATION OF DETECTION ERROR

| $P_{on}$ | $P_{off}$ | $QRS_{on}$ | $QRS_{off}$ | $T_{off}$ |
|---|---|---|---|---|
| 10.2 ms | 12.7 ms | 6.5 ms | 11.6 ms | 30.6 |

In this implementation, ECG signals containing more than 0.32 dB of noise are considered of insufficient quality for further processing (e.g. Q3). If the signal SNR is between 0.32 and 15.35 dB, it is deemed that only reliable QRS detection is possible (e.g. Q2). Full wave analysis is considered desirable if the noise level in the signal is less than 15.35 dB (e.g. Q1). These thresholds can subsequently be applied during processing in the THR block (see FIG. 3).

Figure 7:
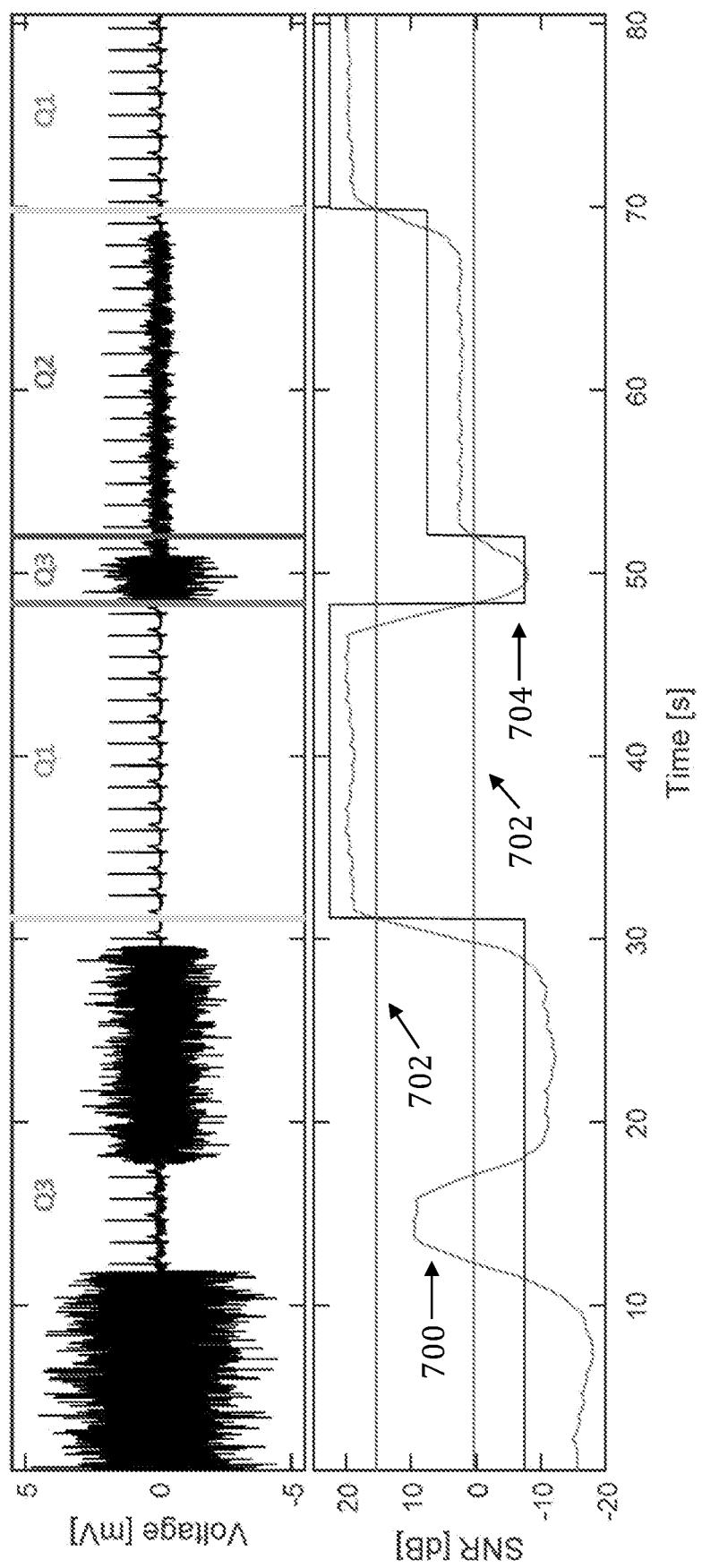
FIG. 7 shows, at the top, an artificial ECG signal with detected segment borders and a continuous SNR curve, two determined thresholds, and final segment distribution.

To illustrate the functionality of such a segmentation scheme, an artificial ECG signal was created, with various levels of noise added. The result of segmentation is shown in FIG. 7. In the upper graph of FIG. 7, an artificial ECG signal with detected segment borders (vertical lines). In the lower graph of FIG. 7, a continuous SNR curve 700, two determined thresholds 702, and final segment distribution 704 are illustrated. In addition to delineating segments of Q1, Q2, and Q3, the correction step excluded a segment of high SNR signal during the initial Q3 segment. Although the quality of this segment is satisfactory, its short-time length precludes further analysis. The short "low-SNR" area between segments Q1 and Q2 was correctly segmented, and thus would not influence full wave analysis in Q1 or QRS detection in Q2. Separately applying different rules to the high-quality and degraded segments is useful to retain only those sections that are suitable for subsequent analysis.

Figure 8:
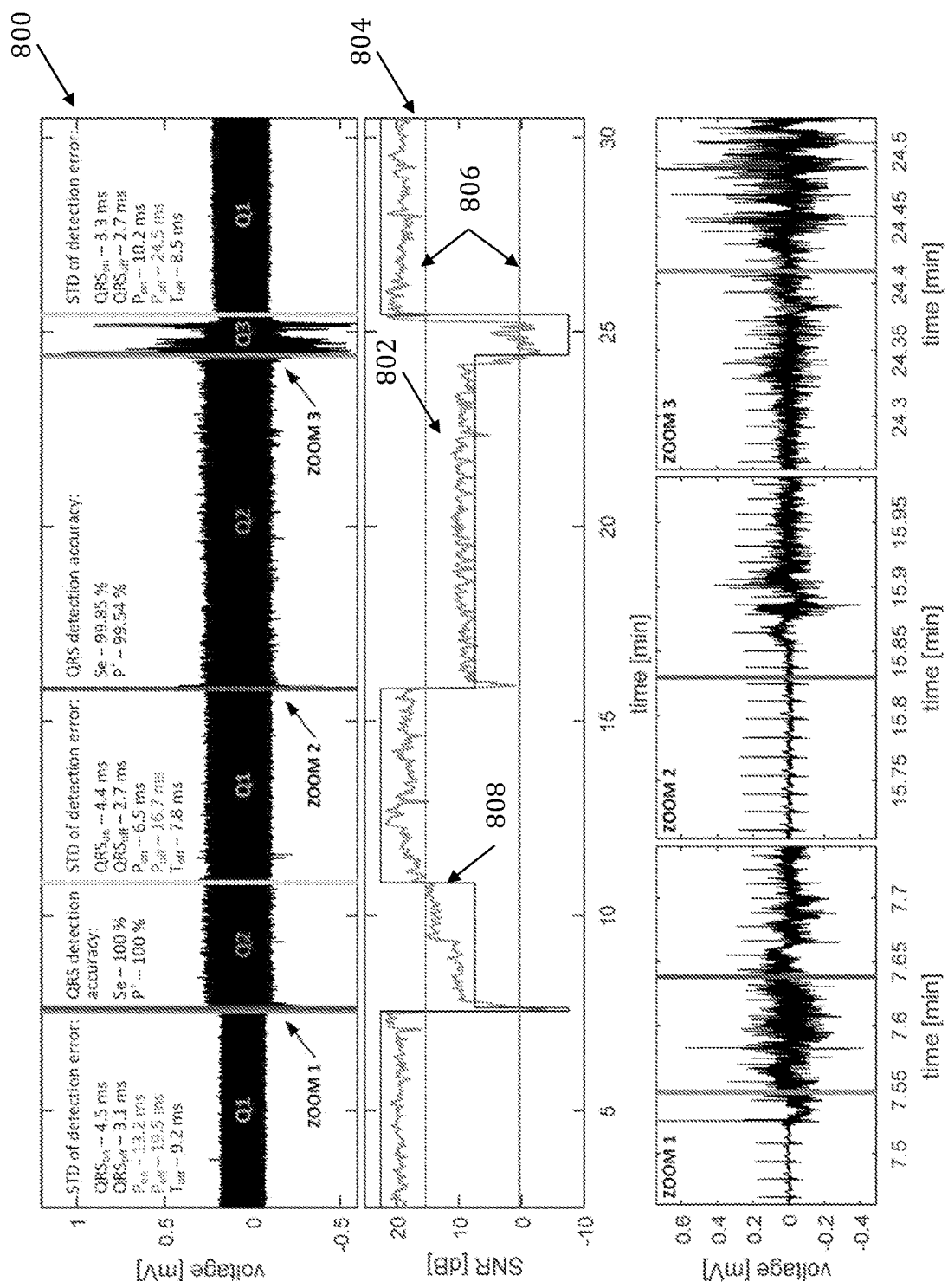
FIG. 8 shows provides correlated graphs of an ECG signal taken from the shoulder, a continuous SNR curve, and three sub-regions of an analyzed ECG.

These methods for SNR calculation and ECG segmentation have been verified using real electrocardiogram data acquired by a wearable physiological monitor. FIG. 8 provides experimental results illustrating an ECG dataset that was recorded as a one-lead signal from the shoulder of an informed-consent subject. The upper panel 800 of FIG. 8 shows 28 minutes of ECG signal recording. During this time the subject was asked to perform different activities. The subject was in the supine position for the first 7.5 minutes, then assumed a sitting position until the 16 minute mark, and a standing position until the 24 minute mark; the subject then performed twenty squats, and at the 25.5 minute mark returned to the supine position. The involvement of different muscle groups in these activities produced different amounts of noise. The amount of noise measured by the continuous SNR curve 802 can be observed in the middle panel 804 of FIG. 8. Block THR (see FIG. 3) is responsible for tracking this noise activity; if the SNR was found to significantly cross one of the thresholds 806 a new segment was initialized, as evident by the change in the level of the tracking line 808. The borders of new segments are marked by vertical color lines in the top panel of FIG. 8. As presented in the lower panel of FIG. 8, new segments are initiated when the noise level changes significantly. Even when the noise level is highly variable throughout the experiment, both detectors (QRS and full wave) are able to annotate the data. The bottom panel of FIG. 8 shows three zoomed-in sub-regions of an analyzed ECG.

An objective evaluation of the segmentation algorithm was also performed. Before starting the automatic segmentation, time points were manually identified to define the beginning of new segments, according to the SNR curve. The automatically determined distribution of quality segments agreed with the assumptions made here to within 99.02%.

Correct classification of the determined segments was verified by the results of QRS complex detection, and by delineation of other significant points within the corresponding segments. The upper panel of FIG. 8 displays the results of QRS detection performed on segments identified as Q2 ("medium" quality); the numbers represent sensitivity and positive predictive value. This result satisfies the assumption for reliable QRS detection as outlined by Köhler et al. in "The principles of software QRS detection," *Engineering in Medicine and Biology Magazine, IEEE*, vol. 21, pp. 42-57, 2002. In segments identified as Q1 (deemed to be of the highest relative quality), full wave analysis was performed. For these segments, the standard deviations of detection error (compared to manual annotation) for five significant points are shown in the top panel of FIG. 8. In most cases, the data satisfied the criteria in Table I; those criteria not met are marked in red.

Data analysis preferably begins with a pre-processing step to characterize data quality, which may be impacted by such factors as improper attachment, sensor failure, and physiologic noise. Exemplary versions of the approaches discussed above need rely only on, and can adapt to, the characteristics of the input signal. Advantageously, these approaches provide the ability to quantitatively select subsequent signal analysis based on the SNR through well-defined limits of detection. The decision rules used can be tailored to target particular waves in the ECG signals depending on SNR. For example, full ECG wave analysis is robust for signals with an estimated SNR of more than 15.35 dB. Because of the small amplitude of P waves, detecting their borders can be challenging. Accordingly, in Q1 segments when the SNR was estimated near 20 dB, the SNR locally measured in the area of the P waves was close to zero dB. Decision rules may be adjusted so as to, for example, specifically target T wave detection at lower SNR, and P wave detection at higher SNR.

There are many clinical and non-clinical health reasons to monitor ECG signals. To do so on a wearable platform is challenging due to the limited available computational, memory, and battery resources. Moreover, the quality of data obtained from a wearable device may vary greatly depending on the sensor, sensor placement, and activity of the person wearing the device. In order to appropriately process the ECG signal and report meaningful findings—e.g. to assess the diagnostic performance across multiple devices or bounds of signal quality in large clinical trial protocol design—it is important to characterize the quality of the signal prior to analysis. The approaches discussed above to estimating the SNR of the signal, in combination with decision rules for selecting appropriate analysis protocols, can facilitate on-board embedded analysis of ECG signals by, for example, small microcontrollers or microprocessors executing the computer code implementation of these algorithms.

Therefore, systems and methods are provided to estimate electrocardiogram signal quality using a local time window by continuous calculation of the ratio between the noise-free signal power and noise power (SNR). This signal quality metric allows not only binary determination between good/bad signals, but also quantification of the quality of specific segments of the signal. The system determines the signal SNR by first estimating a noise-free signal and comparing it to the residual noise component. Following SNR estimation, the signal can be segmented into bins according to the quality level of the data. For example, signals can be quantitatively distinguished according two or more levels of signal quality as indicated by the SNR estimate, such as: signals that contains very low noise levels and are suitable for full ECG wave analysis; signals containing a moderate level of noise that still allow reliable ECG QRS detection; and signals that contain an excessive amount of noise, making that segment undesirable for further processing. The system can be used with readings from any device taking readings, including low-power mobile and wearable devices which may have relatively limited computing power. The system provides distinct advantages for pipelining large amounts of data collected by (for example) wearable devices into tailored data analysis by accounting for high-priority ECG signal features. Additionally, the system facilitates quantification of the maximum possible or allowable noise for reliable QRS detection and delineation of the full ECG waveform. QRS (medium quality) and full ECG (high quality) waveform detection limits in preferred implementations may be set to, for example, 0.32 and 15.35 dB, respectively.

The present invention has been described in terms of one or more preferred embodiments, and it should be appreciated that many equivalents, alternatives, variations, additions, and modifications, aside from those expressly stated, and apart from combining the different features of the foregoing versions in varying ways, can be made and are within the scope of the invention. Following are additional examples. These examples are not to be construed as describing the only additions and modifications to the invention, and the true scope of the invention will be defined by the claims included in any later-filed utility patent application claiming priority from this provisional patent application.

For example, as suggested above, although the discussion has focused on ECGs, alternative versions of the invention can be used to evaluate other physiological signals, such as signals resulting from electroencephalography (EEG) and magnetoencephalography (MEG). Also, although certain advantages have been discussed in particular implementations, such as with wearable ECG devices, the benefits of the invention can be realized in other devices as well, such as high-quality laboratory and clinical equipment, or other devices receiving signals with signal quality levels that potentially vary over time or that are to be monitored. Moreover, although the quality metric discussed above is SNR, other metrics based on signal power, noise power, and/or other readings may also be used. Further, although the discussion above focused on three quality levels, any number of quality levels are permitted, with each quality level deemed suitable for different analyses. Furthermore, the above systems and methods can be implemented using hardware, software, single integrated devices, multiple devices in wired or wireless communication, or any combination thereof.

In various exemplary versions, any signal (i.e., series of measurements) may be taken, and the signal quality estimated by determining a signal quality metric. Based at least in part on the signal quality metric, a decision system may be implemented to make a decision about a subsequent step in the processing/analysis of the signal. The signal may be, for example, any time-varying physiologic signal, examples of which are provided above. In the first step (i.e., estimating signal quality), an estimate of the noise-free signal may be calculated. In the ECG context, the noise-free signal may be estimated by filtering the ECG signal, as discussed above. However, there are alternative approaches.

In certain configurations, the noise-free signal may be based on a stimulus/interrogation signal. For example, in the context of BOLD imaging, the brain may be stimulated with a known temporal pattern of visual (or other sense) stimuli. The signal is recorded, providing an input temporal pattern which can be used to estimate the noise-free signal that is then used to estimate the signal quality. In alternative versions, a noise free signal may be estimated using an available statistical model. For example, statistical models of the cardiovascular and pulmonary components in a PPG signal may be used; such separate statistical models (e.g., rate of variation, occurrence of signal peaks, etc.) can serve as the noise-free signal.

Alternative configurations may use non-temporal equivalents for estimation of the noise-free signal. For example, a prior statistical model of the shape of a tumor may be available. A patient can be scanned using, for example, magnetic resonance (MR), computerized tomography (CT), nuclear medicine (NM), etc. Before using such image data, the quality of the image (which is spatially varying, not temporally varying) may be estimated. The prior statistical model of the shape of the tumor may be used to determine if the imaging has enough signal quality to perform a segmentation of the image.

One example for such an approach involves ultrasound image acquisition. For example, a two-dimensional (2D) B-Mode ultrasound may be used to image a Field of View (a tumor and surrounding vascular structures). Multiple 2D ultrasound images may be used to create a three-dimensional (3D) model. Questions that may arise include, for example, whether there is a sufficient number of 2D images for calculating the volume of the tumor, or whether there are enough images and spatial resolution to segment out the vessel bed. Exemplary systems and methods could use a prior model (such as a segmented CT scan) to determine the quality of the dataset and answer such questions independently.

Regarding the decision system, different algorithms may be used to make a decision about an upcoming processing/analysis step. In the context of ECGs, for example, the decision may involve R-R interval analysis and/or full wave analysis. In the context of PPGs, respiration rate, blood oxygenation computation, and/or heart rate computation, for example, may be used to make a decision. For ultrasound imaging, the decision may involve segmentation, volume estimation, and/or texture measurement, for example. The decision system may use the signal quality estimation to determine which analysis algorithms are appropriate given the input signal. For some PPG signals, for example, it may be possible to obtain respiration and blood oxygenation data, but not heart rate. For an ultrasound system, it may be sufficient to perform volume estimation but not segmentation. The decision system may base this decision on the estimate of the noise-free signal and the estimate of the signal quality.

By way of approximate, non-limiting analogy with respect to certain exemplary versions, the approach may be said to have certain conceptual similarities to the negotiation of baud rates by certain modems. One modem may send a known signal to the other modem, and the other modem may respond back with an estimate of what it heard; this exchange may repeat until an optimal baud rate is chosen. By way of distinction from the modem analogy, however, a signal input may not be needed because the signal itself may be used for determining the signal quality. Also, while the modems are attempting to evaluate the connection between each other, it is not the connection between two points (i.e., the physiologic signal and the sensor) that are being optimized here. Moreover, while the modem aims to provide communication between two end points, here, based on the estimate of signal quality, a choice is made from a collection of different algorithms that yield different results. As another non-limiting analogy with respect to certain exemplary versions, the process may be said to have certain conceptual similarities to a smartphone connecting to a wireless tower. The phone may estimate the signal quality between it and the tower, and based on the quality, the phone may decide, for example, that it can only be used for analog phone calls and text messages, or that it can be used for text-only internet requests and digital calls.

We claim:

1. A method for evaluating signal quality, the method including the steps of:
   a. receiving, by a processor, a physiological signal based on a series of measurements on a subject;
   b. evaluating, by the processor, a quality of the physiological signal received comprising estimating a noise-free signal power and estimating a noise power for the series of measurements; and
   c. basing, by the processor, an analysis of the physiological signal at least in part on the quality evaluation comprising evaluating the signal quality of the series of measurements based on the estimated noise-free signal power and the estimated noise power.

2. The method of claim 1 wherein evaluating a quality of the physiological signal includes estimating a signal quality metric.

3. The method of claim 2 wherein the quality metric is a signal-to-noise ratio of the noise-free signal power to the noise power.

4. The method of claim 2 wherein the noise-free signal is estimated using a stimulus/interrogation signal.

5. The method of claim 4 wherein the physiological signal is a blood oxygenation level dependent (BOLD) imaging signal, and the stimulus/interrogation signal is a neural stimulation signal.

6. The method of claim 5 wherein the neural stimulation signal is a temporal pattern of a sense stimulus.

7. The method of claim 5 wherein the neural stimulation is a known temporal pattern of a visual stimulus.

8. The method of claim 7 further including the step of recording the neural stimulation to estimate the noise-free signal.

9. The method of claim 2 wherein estimating a signal quality metric includes using a statistical model as a noise-free signal.

10. The method of claim 9 wherein the statistical model corresponds with one or more of a rate of variation and an occurrence of signal peaks.

11. The method of claim 9 wherein the statistical model corresponds with the cardiovascular and pulmonary components in a photoplethysmography (PPG) signal.

12. The method of claim 1 wherein the noise-free signal power is estimated using one or more filters.

13. The method of claim 12 wherein the one or more filters includes a Wavelet Wiener Filter.

14. The method of claim 1 wherein basing an analysis of the physiological signal includes selecting between two analyses with different computational demands.

15. The method of claim 1 wherein basing an analysis of the physiological signal includes selecting an analysis algorithm.

16. The method of claim 15 wherein the physiological signal is an electrocardiography (ECG) signal, and the analysis algorithm includes at least one of an R-R interval analysis and a full-wave analysis.

17. The method of claim 15 wherein the physiological signal is a photoplethysmography (PPG) signal, and wherein the analysis algorithm is based at least in part on one or more of a respiration rate, a blood oxygenation computation, and a heart rate computation.

18. The method of claim 15 wherein the physiological signal is an ultrasound imaging signal, and wherein the analysis algorithm is based at least in part on one or more of a segmentation, a volume estimation, and a texture measurement.

19. The method of claim 1 wherein physiological signal is time-varying.

20. The method of claim 1 wherein physiological signal is spatially-varying.

* * * * *